United States Patent [19]

Dhar et al.

[11] Patent Number: 4,803,204

[45] Date of Patent: Feb. 7, 1989

[54] 1-SUBSTITUTED 3-ARYL-7-CHLORO-3,4-DIHYDRO(2H)-ACRIDONE N-OXIDES, A PROCESS FOR THEIR PREPARATION, AND THEIR USE AS MEDICAMENTS AND FEEDSTUFF ADDITIVES

[75] Inventors: Rajkumar Dhar; Bindumadhavan Venugopalan; Dipak K. Chatterjee; Richard H. Rupp; Noel J. de Souza, all of Bombay, India

[73] Assignee: Hoechst Aktiengesellschaft, Frankfurt am Main, Fed. Rep. of Germany

[21] Appl. No.: 75,643

[22] Filed: Jul. 20, 1987

[30] Foreign Application Priority Data

Jul. 22, 1986 [DE] Fed. Rep. of Germany ....... 3624702

[51] Int. Cl.$^4$ .................... A61K 31/47; C07D 219/06; C07D 219/08
[52] U.S. Cl. .................. 514/232.8; 514/255; 514/212; 514/297; 540/597; 544/126; 544/361; 546/103
[58] Field of Search ................. 546/103; 514/297, 255, 514/212, 239, 232.8; 544/361, 126; 540/597

[56] References Cited

U.S. PATENT DOCUMENTS

| | | | |
|---|---|---|---|
| 3,947,449 | 3/1976 | Durckheimer et al. | 546/103 |
| 4,260,615 | 4/1981 | Raether et al. | 514/297 |
| 4,291,034 | 9/1981 | Werbel | 546/103 X |
| 4,593,027 | 6/1986 | Winklemann et al. | 514/253 |

FOREIGN PATENT DOCUMENTS

3410517 A1  9/1985  Fed. Rep. of Germany .

OTHER PUBLICATIONS

Albert, "The Acridines", 2nd Ed., N.Y., St. Martin's Press (1966), pp. 376-377.
Winkelmann et al., Arzneim.-Forsch., vol. 37(6), pp. 647-661 (6/87).
Winkelmann et al., Chemical Abstracts, vol. 107:108835t (1987).
Durckheimer et al., Arzneimittelforschung, Drug Research 30(11), No. 7, pp. 1041-1046 (1980).
Werbel et al., Eur. J. Med. Chem., Chim. Ther. 20, No. 4, pp. 363-370 (1985).

*Primary Examiner*—Donald G. Daus
*Assistant Examiner*—Diana G. Rivers
*Attorney, Agent, or Firm*—Finnegan, Henderson, Farabow, Garrett, & Dunner

[57] ABSTRACT

The present invention relates to novel, 1-substituted 3-aryl-7-chloro-3,4-dihydro-(2H)-acridone N-oxides, a process for their preparation, pharmaceutical compositions containing these compounds, and their use as chemotherapeutic agents, in particular as antimalarials and coccidiostatics.

7 Claims, No Drawings

1-SUBSTITUTED 3-ARYL-7-CHLORO-3,4-DIHYDRO(2H)-ACRIDONE N-OXIDES, A PROCESS FOR THEIR PREPARATION, AND THEIR USE AS MEDICAMENTS AND FEEDSTUFF ADDITIVES

The present invention relates to novel, 1-substituted 3-aryl-7-chloro-3,4-dihydro-(2H)-acridone N-oxides, a process for their preparation, pharmaceutical compositions containing these compounds, and their use as chemotherapeutic agents, in particular as antimalarials and coccidiostatics.

The following patents and publications relate to 3-aryl-7-chloro-3,4-dihydro-10-hydroxy-1,9(2H,10H)-acridinedione and the derivatives thereof:

German Pat. No. 2,337,474
German Offenlegungsschrift No. 2,748,333
Arzneimittelforschung, Drug Research 30(11), No. 7, pp. 1041–46 (1980)
Eur. J. Med. Chem., CHIM. THER. 20 No. 4, pp. 363–370 (1985).

Some of the acridones described have a chemotherapeutic action against protozoa infections.

The compounds according to the invention have hitherto not been described in the literature. They differ in constitution from the compounds known from the prior art in that they represent N-oxides of the acridone molecule and carry alkoxy or substituted amino substituents in the 1-position. The compounds according to the invention are extremely active against malaria and coccidia parasites.

Since malaria parasites rapidly build up resistance against the medicaments which are conventionally used, there is a requirement for new, reliable and effective antimalarials.

The present invention is a result of attempts to develop novel compounds having a high activity against malaria without undesired side effects.

The present invention therefore relates to 1-substituted 3-aryl-7-chloro-3,4-dihydro-2(H)-acridone N-oxides of the formula I

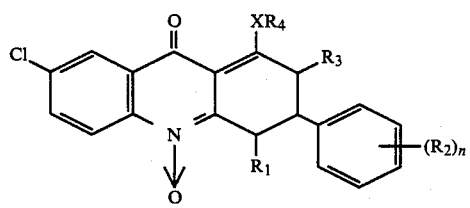

I in which $R_1$ and $R_3$ are identical or different and represent hydrogen, $C_1$–$C_4$-alkyl or a $C_2$–$C_5$-carbalkoxy or aryl group, $R_2$ denotes halogen or trifluoromethyl, where the substituents, if n denotes the number 2 or 3, may be identical or different, n represents a number from 0 to 3, X represents oxygen or nitrogen, and $R_4$, if X denotes oxygen, represents a straight-chain or branched $C_1$–$C_4$-alkyl group, or if X denotes nitrogen, $XR_4$ represents a di-$C_1$–$C_4$-alkylamino group or a five- or six-membered heterocyclic ring, which may contain a further heteroatom and is optionally monosubstituted or polysubstituted by $C_1$–$C_4$-alkyl, by substituted $C_1$–$C_4$-alkyl or by an aryl group which is optionally monosubstituted or polysubstituted by $C_1$–$C_4$-alkyl, $C_1$–$C_4$-alkoxy or halogen.

When $R_1$ or $R_4$ denotes a $C_1$–$C_4$-alkyl group, it is a methyl, ethyl, propyl, isopropyl or butyl group.

If $R_2$ represents halogen, it denotes chlorine, bromine, fluorine or iodine.

As a $C_2$–$C_5$-carbalkoxy group, $R_1$ and $R_3$ preferably denote carbomethoxy or carboethoxy.

A dialkylamino group $XR_4$ is preferably a dimethylamino or diethylamino group.

$C_1$–$C_4$-Alkoxy is preferably taken to mean the methoxy or ethoxy group.

If $XR_4$ represents a five- or six-membered heterocyclic ring, this is preferably a heterocyclic ring such as pyrrolidino, piperidino, morpholino or piperazino, which is optionally substituted by $C_1$–$C_4$-alkyl, or an aryl group whih may be monosubstituted or polysubstituted, if appropriate, by $C_1$–$C_4$-alkyl, halogen, $C_1$–$C_4$-alkoxy or trifluoromethyl. Alkyl, halogen and alkoxy here have the same meaning as given above. Aryl is preferably taken to mean phenyl.

Compounds of the formula I in which $R_1$ represents hydrogen, $R_3$ represents hydrogen or methyl, $R_2$ represents chlorine or a trifluoromethyl group, X represents oxygen or nitrogen and $R_4$ represents methyl, ethyl or isopropyl, or $XR_4$ represents an optionally substituted piperazino, piperidino or pyrrolidino radical, and n is 1 are preferred.

Particularly preferred compounds according to the invention are:

7-chloro-3,4-dihydro-1-methoxy-3-(4-trifluoromethylphenyl)-2(H)-acridone N-oxide monohydrate, 7-chloro-3,4-dihydro-1-ethoxy-3-(4-trifluoromethylphenyl)-2(H)-acridone N-oxide sesquihydrate, 7-chloro-3,4-dihydro-1-isopropoxy-3-(4-trifluoromethylphenyl)-2(H)-acridone, N-oxide, 7-chloro-3,4-dihydro-1-ethoxy-2-methyl-3-(4-trifluoromethylphenyl)-2(H)-acridone N-oxide dihydrate, 7-chloro-3,4-dihydro-2-methyl-1-(N-methylpiperazino)-3-(4-trifluoromethylphenyl)-2(H)-acridone N-oxide monohydrate, 7-chloro-3,4-dihydro-1-pyrrolidino-3-(4-trifluoromethylphenyl)-2(H)-acridone N-oxide monohydrate, 7-chloro-3,4-dihydro-1-(N-2,6-dimethylphenylpiperazino)-3-(4-trifluoromethylphenyl)-2(H)-acridone N-oxide monohydrate, 7-chloro-3,4-dihydro-1-(N-4-methoxyphenylpiperazino)-3-(4-trifluoromethylphenyl)-2(H)-acridone N-oxide monohydrate, 7-chloro-3,4-dihydro-1-[N-(N'-benzylpiperazino)]-3-(4-trifluoromethylphenyl)-2(H)-acridone N-oxide monohydrate, 7-chloro-3,4-dihydro-1-(N-phenylpiperazino)-3-(4-trifluoromethylphenyl)-2(H)-acridone N-oxide monohydrate, 7-chloro-3,4-dihydro-1-(N-3-trifluoromethylphenylpiperazino)-3-(4-trifluoromethylphenyl)-2(H)-acridone N-oxide monohydrate, 7-chloro-3,4-dihydro-1-morpholino-3-(4-trifluoromethylphenyl)-2(H)-acridone N-oxide monohydrate, 7-chloro-3,4-dihydro-1-[N-2-methoxyphenylpiperazino]-3-(4-chlorophenyl)-2(H)-acridone N-oxide, 7-chloro-3,4-dihydro-1-(N-methylpiperazino)-3-(4-trifluoromethylphenyl)-2(H)-acridone N-oxide monohydrate, 7-chloro-3,4-dihydro-1-[N-(2-methyl-N'-phenylpiperazino)]-3-(4-trifluoromethylphenyl)-2(H)-acridone N-oxide monohydrate, 7-chloro-3,4-dihydro-1-[N-(N'-2-methylphenyl-piperazino)]-3-(4-trifluoromethylphenyl)-2(H)-acridone N-oxide monohydrate and 7-chloro-3,4-dihydro-1-[(N-4-(p-chlorophenyl)-3-methylpiperazino]-3-(4-trifluoromethylphenyl)-2(H)-acridone N-oxide monohydrate.

Some of the new N-oxides according to the invention are listed in Table I below.

| $R_1$ | $R_2$ | $R_3$ | $XR_4$ | Y | Melting point |
|---|---|---|---|---|---|
| H | Cl | H | pyrrolidino | — | >300 |
| H | Cl | H | hexamethyleneimino | — | 222–23 |
| H | Cl | H | 4-(3-trifluoromethylphenyl)piperazino | $H_2O$ | 197–200 |
| H | Cl | H | 4-methylpiperazino | — | 220–22 |
| H | Cl | H | 4-(2-methoxyphenyl)piperazino | — | 188–89 |
| H | Cl | H | 2-methylpiperidino | 1.5 $H_2O$ | 200–201 |
| H | Cl | H | 4-methylpiperidino | $H_2O$ | 215–216 |
| H | Cl | H | morpholino | $H_2O$ | 250 (decomp.) |
| H | $CF_3$ | H | pyrrolidino | $H_2O$ | 215 (decomp.) |

-continued
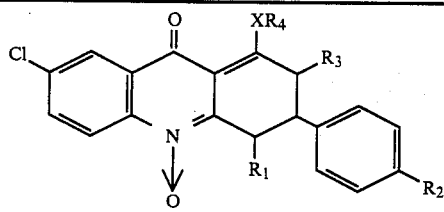
| R₁ | R₂ | R₃ | XR₄ | Y | Melting point |
|---|---|---|---|---|---|
| H | CF₃ | H | 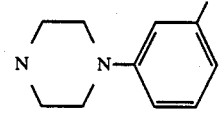 | H₂O | 210–11 |
| H | CF₃ | H | N(CH₃)₂ | H₂O | 230 |
| H | CF₃ | H | 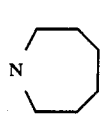 | 1.5 H₂O | 220–25 |
| H | CF₃ | H | 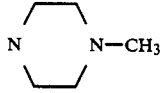 | H₂O | 215–220 |
| H | CF₃ | H | 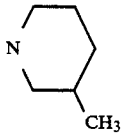 | H₂O | 205—205 |
| H | CF₃ | H | 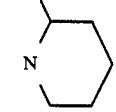 | H₂O | 205–206 |
| H | CF₃ | H | 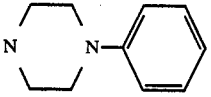 | H₂O | 197–98 |
| H | CF₃ | H | 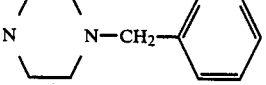 | H₂O | 199–200 |
| H | CF₃ | H | 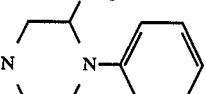 | H₂O | 209–210 |
| H | CF₃ | H | 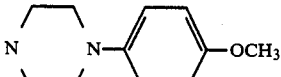 | H₂O | 204–5 |
| H | CF₃ | H | 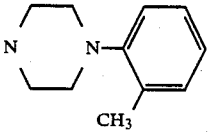 | H₂O | 212–13 |

-continued

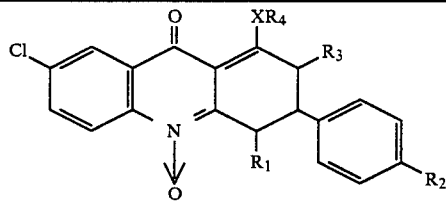

| R₁ | R₂ | R₃ | XR₄ | Y | Melting point |
|---|---|---|---|---|---|
| H | CF₃ | H | (piperazine)-N-(4-chlorophenyl with CH₃) | H₂O | 207–8 |
| H | CF₃ | H | (piperazine)-N-CH(CH₃)-phenyl | H₂O | 184–85 |
| H | CF₃ | H | (piperazine)-N-(3,4-dimethylphenyl) | H₂O | 209–10 |
| H | CF₃ | H | (piperazine)-N-(2,6-dimethylphenyl) | H₂O | 221–22 |
| H | CF₃ | H | (piperazine)-N-(4-tert-butylphenyl) | H₂O | 203–4 |
| H | CF₃ | H | 4-methylpiperidine | H₂O | 203–4 |
| H | CF₃ | H | (piperazine)-N-(2-methoxyphenyl) | — | 214–215 |
| H | CF₃ | H | morpholine | H₂O | 230–36 |
| H | CF₃ | CH₃ | 4-methylpiperazine | H₂O | 290–92 |
| H | CF₃ | H | OCH(CH₃)₂ | — | >300 |
| H | CF₃ | H | OCH₃ | H₂O | 292–94 |
| H | CF₃ | H | OC₂H₅ | 2.5 H₂O | >300 |
| H | CF₃ | CH₃ | OC₂H₅ | 2. H₂O | 296 |
| H | CF₃ | C₆H₅ | OC₂H₅ | — | >300 |

The present invention furthermore relates to a process for the preparation of the compounds of the for-

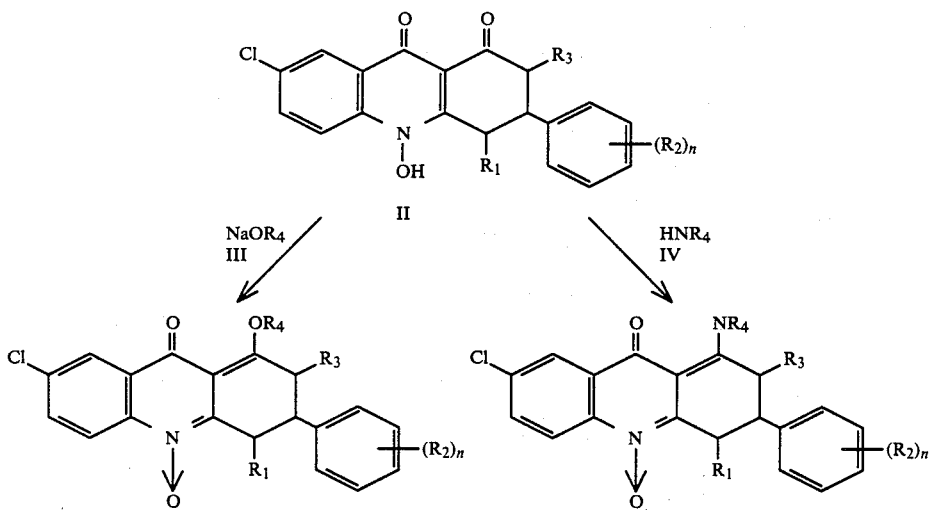

in which $R_1$ to $R_4$ and n have the abovementioned meanings. Under preferred conditions, alcoholic solvents and room temperature are used.

The starting acridones of the formula (II) can be prepared in a fashion analogous to that described in German Pat. No. 2,337,474 and in Arzneimittelforschung, Drug Research 30 (II), No. 7, pp. 363–370 (1980) and illustrated by the following equation I.

Equation I

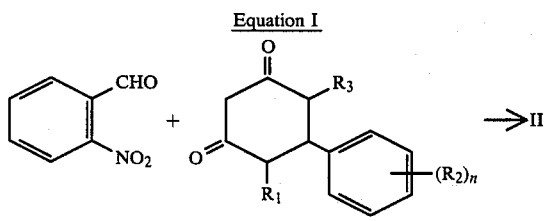

in which $R_1$, $R_2$ and $R_3$ have the abovementioned meanings. The compounds (I) can be recrystallized from organic solvents, such as chloroform, methanol or acetone, or purified by trituration in these solvents.

The compounds according to the invention have valuable chemotherapeutic properties which are suitable for combating protozoa infections. For example, they are distinguished by a high activity against Plasmodia, the malaria parasites. It was also possible to demonstrate an activity against the chloroquin-resistant strain of Plasmodium berghei, using suitable models. Parasitemia, for example, is completely cured on administration in a dose in the range 10–25 mg/kg×5 to mice infected with Plasmodium berghei.

The compounds of the formula I can be administered per-orally or parenterally in dosages in the range from 2.5 to 100 mg/kg of body weight. As antimalarials, dose unit forms such as coated tablets or capsules for oral administration or solutions or suspensions for injections, in each case containing 100 to 400 mg of active ingredient, are preferred. Such dose units are administered once to three times daily, depending on the health of the patient.

The present invention furthermore relates to pharmaceutical preparations which contain a compound according to the invention mixed or together with a pharmaceutically suitable excipient. The preparations can exist in a form suitable for oral or parenteral administration and preferably in dose unit forms.

For oral administrations, tablets, coated tablets, capsules, powders or granules which contain the active ingredient mixed with or together with, for example, starch, cellulose powder, talcum, magnesium stearate, sugar, gelatin, calcium carbonate, finely disperse silica or carboxymethylcellulose are suitable.

For parenteral administration, in particular for intramuscular injections, sterile suspensions, for example oily suspensions prepared using sesame oil, castor oil or synthetic triglycerides, if appropriate with simultaneous use of surfactants, for example sorbitan fatty acid esters, are suitable. In addition, aqueous suspensions can be prepared, for example using ethoxylated sorbitan fatty acid esters, if appropriate with the addition of thickening agents, for example polyethylene glycol or carboxymethylcellulose.

In addition, the compounds according to the invention are also active against coccidiosis parasites, for example poultry, turkey, rabbit, cattle and pig coccidiasis. In modern raising methods for animals for slaughtering, coccidiosis represents a serious problem during the rearing and fattening period since it can cause considerable economic losses. Accordingly, there is great interest in the availability of highly active, readily tolerated coccidiostatics.

To this purpose, the compounds of the formula I are administered mixed with suitable feedstuffs. The invention accordingly also relates to a feedstuff additive which contains a compound of the formula I.

The following examples illustrate the invention.

PREPARATION EXAMPLES

EXAMPLE 1

7-Chloro-3,4-dihydro-1-pyrrolidno-3-(4-trifluoromethylphenyl)-2(H)-acridone N-oxide monohydrate A suspension of 7-chloro-3,4-dihydro-10-hydroxy-3-(4-trifluoromethylphenyl)-1,9(2H,10H)-acridone (1.02 g, 0.0025 mol) in methanol (10 ml) is stirred at room temperature, and pyrrolidine (0.22 ml, 0.0032 mol) is added dropwise, a clear solution forming. On further stirring, a yellow precipitate appears in the reaction mixture, and the latter is stirred for a further half an hour and then filtered. The product obtained here is washed with acetone and dried in vacuo, 7-chloro-3,4-dihydro-1-pyrrolidino-3-(4-trifluoromethylphenyl)-acridone N-oxide monohydrate of melting point 215° C. being obtained in 78% yield (0.9 g).

The following compounds are prepared under the conditions described above and using an appropriately substituted acridinedione and the appropriate amine in place of pyrrolidine:

7-chloro-3,4-dihydro-1-(N-2,6-dimethylphenyl-piperazino)-3-(4-trifluoromethylphenyl)-2(H)-acridone N-oxide monohydrate, melting point 221°–22° C.;

7-chloro-3,4-dihydro-1-(N-4-methoxyphenyl-piperazino)-3-(4-trifluoromethylphenyl)-2(H)-acridone N-oxide monohydrate, melting point 204°–5° C.;

7-chloro-3,4-dihydro-1-[N-(N-benzylpiperazino)]-3-(4-trifluoromethylphenyl)-2(H)-acridone N-oxide monohydrate;

7-chloro-3,4-dihydro-1-(N-phenylpiperazino)-3-(4-trifluoromethylphenyl)-2(H)-acridone N-oxide monohydrate, melting point 197°–98° C.;

7-chloro-3,4-dihydro-1-(N-3-trifluoromethylphenyl-piperazino)-3-(4-trifluoromethylphenyl)-2(H)-acridone N-oxide monohydrate, melting point 210°–11° C.;

7-chloro-3,4-dihydro-1-(morpholino)-3-(4-trifluoromethylphenyl)-2(H)-acridone N-oxide monohydrate, melting point 250° C. (decomp.);

7-chloro-3,4-dihydro-1-[N-2-methoxyphenyl-piperazino]-3-(4-chlorophenyl)-2(H)-acridone N-oxide, melting point 188°–89° C.;

7-chloro-3,4-dihydro-1-(N-methylpiperazino)-3-(4-trifluoromethylphenyl)-2(H)-acridone N-oxide monohydrate, melting point 215°–20° C.;

7-chloro-3,4-dihydro-1-[N-2-methyl-N'-phenyl-piperazino]-3-(4-trifluoromethylphenyl)-2(H)-acridone N-oxide monohydrate, melting point 209°–210° C.;

7-chloro-3,4-dihydro-1-[N-4-(p-chlorophenyl)-3-methylpiperazino]-3-(4-trifluoromethylphenyl)-2(H)-acridone N-oxide monohydrate, melting point 207°–208° C.;

7-chloro-3,4-dihydro-2-methyl-1-(N-methyl-piperazino)-3-(4-trifluoromethylphenyl)-2(H)-acridone N-oxide monohydrate, melting point 290°–92° C.

EXAMPLE 2

7-Chloro-3,4-dihydro-1-methoxy-3-(4-trifluoromethylphenyl)-2(H)-acridone N-oxide monohydrate With vigorous stirring, 7-chloro-3,4-dihydro-10-hydroxy-3-(4-trifluoromethylphenyl)-1,9(2H,10H)-acridinedione (10.0 g) is added to a sodium methylate solution prepared by dissolving sodium (1.2 g) in anhydrous methanol (100 ml), the mixture is then stirred for a further one hour at room temperature, and the solution is filtered in order to remove the precipitate. The latter is washed thoroughly with methanol and dried in vacuo, 7-chloro-3,4-dihydro-1-methoxy-3-(4-trifluoromethylphenyl)-2(H)-acridone N-oxide monohydrate of melting point 292°–94° C. being obtained.

The following compounds are prepared under the conditions described above and starting from an appropriately substituted acridinedione and a suitable sodium alcoholate prepared by dissolving sodium in the appropriate alcohol:

7-chloro-3,4-dihydro-1-ethoxy-3-(4-trifluoromethylphenyl)-2(H)-acridone N-oxide sesquihydrate, melting point >300° C.;

7-chloro-3,4-dihydro-1-isopropoxy-3-(4-trifluoromethylphenyl)-2(H)-acridone N-oxide monohydrate, melting point >300° C.;

7-chloro-3,4-dihydro-1-ethoxy-2-methyl-3-(4-trifluoromethylphenyl)-2(H)-acridone N-oxide, melting point 292° C. and 7-chloro-3,4-dihydro-1-ethoxy-2-phenyl-3-(4-trifluoromethylphenyl)-2(H)-acridone N-oxide, melting point >300° C.

We claim:

1. A compound of the formula I

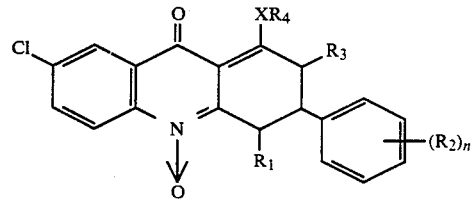

in which $R_1$ and $R_3$, which are identical or different, are hydrogen, $C_1$–$C_4$-alkyl, $C_2$–$C_5$-carbalkoxy, phenyl, or phenyl which is monosubstituted or polysubstituted by $C_1$–$C_4$-alkyl, halogen or amino, $R_2$ is halogen or trifluoromethyl, wherein the substituents are identical or different if n is the integer 2 or 3, n is an integer from 0 to 3, X is oxygen or nitrogen, $R_4$, if X is oxygen, is $C_1$–$C_4$-alkyl or, if X is nitrogen, $XR_4$ is di-$C_1$–$C_4$-alkylamino, a 5- or 6-membered nitrogen heterocyclic ring or a 5- or 6-membered nitrogen heterocyclic ring which contains a further nitrogen or oxygen atom and is unsubstituted or monosubstituted or polysubstituted by $C_1$–$C_4$-alkyl, by substituted $C_1$–$C_4$-alkyl, by phenyl or by phenyl which is itself monosubstituted or polysubstituted by $C_1$–$C_4$-alkyl, $C_1$–$C_4$-alkoxy or halogen.

2. A compound of the formula I as claimed in claim 1, in which:

$R_1$ is hydrogen, $R_2$ is chlorine or trifluoromethyl, n is the integer 1, $R_3$ is hydrogen or methyl, X is oxygen or nitrogen, $R_4$, if X is oxygen, is methyl, ethyl or isopropyl or, if X is nitrogen, $XR_4$ is unsubstituted or substituted piperazino, piperidino or pyrrolidino.

3. A pharmaceutical composition which contains an amount effective as a pharmaceutical in the therapy of a mammal of a compound of the formula I as claimed in claim 1 and a pharmaceutically acceptable carrier.

4. A feedstuff additive which contains a chemotherapeutic amount effective against protozoa infections of a compound as claimed in claim 1 as active ingredient.

5. A method for treating protozoa infections in a mammal which comprises administering an effective amount of a compound as claimed in claim 1.

6. A method for treating malaria in a mammal which comprises administering an effective amount of a compound as claimed in claim 1.

7. A method for the prevention and combating of coccidiosis in productive animals which comprises administering a feedstuff additive containing an effective amount of a compound as claimed in claim 1.

* * * * *